(12) United States Patent
Hur et al.

(10) Patent No.: US 9,115,334 B2
(45) Date of Patent: Aug. 25, 2015

(54) METHOD FOR PRODUCING OMEGA FATTY ACID-CONTAINING EXTRACT FROM PLANT USING SUPERCRITICAL CARBON DIOXIDE EXTRACTION

(75) Inventors: Cheol Goo Hur, Daejeon (KR); Duck Sun Park, Masan-si (KR); Hyo Nam Park, Jinju-si (KR); Jong Soon Lee, Daejeon (KR); Hwang Yong Lee, Seoul (KR)

(73) Assignees: Korea Research Institute of Bioscience and Biotechnology, Daejeon (KR); SUNGJIN FOOD CO., LTD., Gyeongsangnam-do (KR)

(*) Notice: Subject to any disclaimer, the term of this patent is extended or adjusted under 35 U.S.C. 154(b) by 116 days.

(21) Appl. No.: 13/696,060

(22) PCT Filed: May 3, 2011

(86) PCT No.: PCT/KR2011/003294
§ 371 (c)(1),
(2), (4) Date: Nov. 2, 2012

(87) PCT Pub. No.: WO2011/139067
PCT Pub. Date: Nov. 10, 2011

(65) Prior Publication Data
US 2013/0053443 A1 Feb. 28, 2013

(30) Foreign Application Priority Data
May 4, 2010 (KR) .................. 10-2010-0041688

(51) Int. Cl.
*C11B 1/10* (2006.01)
*A23L 1/30* (2006.01)
*A61K 9/20* (2006.01)
(Continued)

(52) U.S. Cl.
CPC .............. *C11B 1/104* (2013.01); *A23L 1/3008* (2013.01); *A61K 9/2018* (2013.01); *A61K 9/2059* (2013.01); *A61K 36/185* (2013.01);
(Continued)

(58) Field of Classification Search
None
See application file for complete search history.

(56) References Cited

U.S. PATENT DOCUMENTS

2006/0252949 A1* 11/2006 Chordia et al. .......... 554/8
2011/0091947 A1 4/2011 Kim et al.

FOREIGN PATENT DOCUMENTS

KR 1005583820000 * 3/2006 ............ A61K 36/16
KR 10-2009-0132048 A 12/2009

OTHER PUBLICATIONS

KR 1005583820000, Yoo, K., et al., A method of manufacturing gingko leaf extract using supercritical fluid extraction, 2006, English translation, 16 pages.*

(Continued)

*Primary Examiner* — Yate K Cutliff
(74) *Attorney, Agent, or Firm* — The PL Law Group, PLLC

(57) ABSTRACT

The present invention relates to a method for preparing an extract containing omega fatty acids from a plant containing omega fatty acids, including the following steps: drying the plant containing omega fatty acids to prepare a powder; and extracting omega fatty acids from the prepared plant powder by using supercritical carbon dioxide as a solvent at an optimum temperature and pressure, a dietary supplement and a cholesterol-lowering pharmaceutical composition containing plant-derived omega fatty acids extracted by the method, and omega fatty acids-containing plant extract containing a predetermined or greater amount of omega-3 fatty acids.

8 Claims, 1 Drawing Sheet

(51) Int. Cl.
*C11B 1/04* (2006.01)
*A61K 36/185* (2006.01)
*A61K 36/535* (2006.01)

(52) U.S. Cl.
CPC ............... *A61K36/535* (2013.01); *C11B 1/04* (2013.01); *A23V 2002/00* (2013.01); *A61K 2236/37* (2013.01)

(56) References Cited

OTHER PUBLICATIONS

Lee, M., et al., The effects of supercritical carbon dioxide on the extraction of perilla oil, 2006, J. Korean Soc Food Sci Nutr, 35(10) pp. 1439-1443.*

Dhole J.A., et al., Prelimnary phytochemical analysis and antimicirobial activity of some weeds collected form Marathwada region, May 3, 2011, Journal of Research in Biology, vol. 1, No. 2, pp. 19-23.*

Ross, I. A., et al., *Portulaca oleracea*, 2003, Medicinal Plants and Weeds, Chapter 23, vol. 1, 11 pages.*

Shin, H., et al., Lipid composition of Perilla seed, 1994, JAOCS, vol. 71, No. 6, pp. 619-622.*

Popp, M. et al., Sample preservatin for determinatin of organic compounds: microwave versus freeze-drying, 1996, Journal of Experimental Botany, vol. 47, No. 303. pp. 1469-1473.*

International Search Report for PCT/KR2011/003294.

Cho, Y.-J. et al. "Biological and Antimicrobial Activity of *Portulaca oleracea*" J. Kor. Soc. Appl. Chem. vol. 51, No. 1 pp. 49-54, Mar. 31, 2008.

* cited by examiner

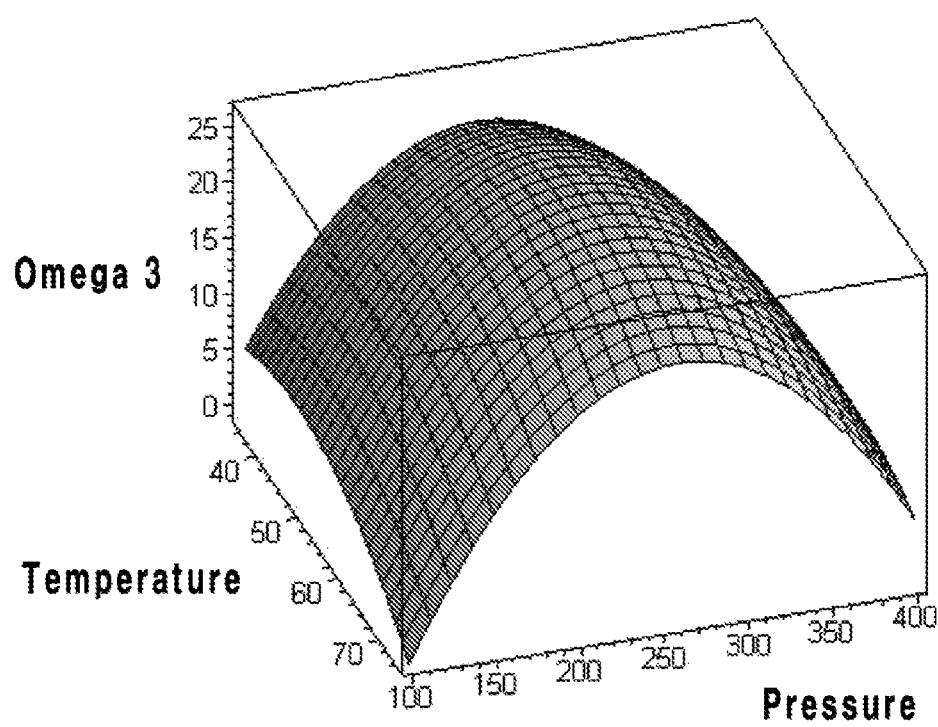

METHOD FOR PRODUCING OMEGA FATTY ACID-CONTAINING EXTRACT FROM PLANT USING SUPERCRITICAL CARBON DIOXIDE EXTRACTION

CROSS REFERENCE TO RELATED APPLICATIONS AND CLAIM OF PRIORITY

This patent application is a National Phase application under 35 U.S.C. §371 of International Application No. PCT/KR2011/003294, filed on May 3, 2011, entitled METHOD FOR PRODUCING OMEGA FATTY ACID-CONTAINING EXTRACT FROM PLANT USING SUPERCRITICAL CARBON DIOXIDE EXTRACTION, which claims priority to Korean Patent Application number 10-2010-0041688, filed May 4, 2010, entire contents of which are incorporated herein by reference.

TECHNICAL FIELD

The present invention relates to a method of producing an omega fatty acid-containing extract from an omega fatty acid-containing plant, wherein the method includes drying an omega fatty acid-containing plant to prepare powder thereof; and extracting an omega fatty acid from the prepared plant powder using supercritical carbon dioxide as a solvent at an optimal temperature and at an optimal pressure, a health functional food including a plant-derived omega fatty acid that is extracted by using the method, a pharmaceutical composition for decreasing the level of cholesterol which includes a plant-derived omega fatty acid that is extracted by using the method, and an omega fatty acid-containing plant extract in which an amount of omega-3 fatty acid is equal to or greater than a predetermined level.

BACKGROUND

*Portulaca oleracea* L. is an annual plant, is also referred to as Oh-hang-cho, Chang-myeong-chae, Ma-chi-chae, or the like, often grows along roadsides, and in vegetable patches and unoccupied lands, and is an edible thickleaf plant. *Portulaca oleracea* L. is distributed around the world, and in Korea, in the summer, a soft portion thereof is blanched in boiling water and dried, and, in the winter, the dried plant is seasoned as a side dish. As for a folk remedy, *Portulaca oleracea* L. has been used as an antidote, a preservative, an antiscorbutic agent, an anticonvulsant, a diuretic, an anthelmintic agent, or a skin sedative, and additionally, its muscle relaxation activity, and antibacterial, anticancer, and antioxidative effects are also known. *Portulaca oleracea* L. consists of L-noradrenalin, dopamine, dopa and various organic acids, aminoacids, and terphene glycoside (portuloside A), and high concentration of omega-3 fatty acid, such as a linolenic acid.

Perilla is an annual herbaceous plant that is produced in many Asian countries including Korea, China, and Japan, and contains various useful components. Due to the inclusion of useful components, *perilla* is used as a pharmaceutical crop, an oilseed crop, and a leaf vegetable. That is, the seed of *perilla* is rich in an alpha-linolenic acid, which is an omega-3 fatty acid, and due to the alpha-linolenic acid, *perilla* has various body modulation functions: for example, brain activities are promoted, synthesis of eicosanoid that causes adult disease, such as high blood pressure or allergic disease, is suppressed, learning abilities are improved, and lifespans are prolonged. Thus, the seed is, as the whole seed, used in a *perilla* tea or confections, and an oil extracted from the seed is used for edible food, pharmaceutical, and industrial purposes.

Methods for creating highly added values by using *perilla* and *Portulaca oleracea* L. having such components and efficacies have not yet been sufficiently developed. Accordingly, a technology that utilizes a great amount of *perilla* and *Portulaca oleracea* L. needs to be developed.

An omega-3 fatty acid is an unsaturated fatty acid included in an external blue colored fish, and examples thereof are EPA, DHA, a linolenic acid, etc. The omega-3 fatty acid is not synthesized in vivo and thus needed to be obtained from foods. DHA is a major component of brain cells and occupies about 10% of a brain cell membrane lipid, and aids information transfer energy metabolism, which is necessarily required for brain cell activities, protein synthesis, memorization, and learning abilities, and prevents brain disorders. Also, DHA suppresses platelet aggregation and extends a blood coagulation time to prevent generation of blood clots, and thus, DHA is effective for the prevention of circulatory disease, such as stroke, heart disease, arteriosclerosis, or high blood pressure. Also, it is reported that DHA lowers the levels of blood cholesterol and neutral fat to prevent blood clots and strengthen blood vessels, thereby causing smooth blood circulation and preventing circulatory disease, such as high blood pressure, or arteriosclerosis. It is also reported that omega-3 decreases the level of low-density lipoproteins (LDL), which is a bad cholesterol, and increases the level of high-density lipoproteins (HDL), which is a good cholesterol.

When typical extraction and purification methods are used, extraction amounts of enriched materials are very high. However, the enriched materials may also include other unnecessary components. Also, the methods require use of various organic solvents that are harmful for the human body, and thus, the residual solvent may highly likely remain in the target extract. Also, the amounts of organic solvents used in the methods are high, thereby increasing the production costs and causing environmental pollutions.

A supercritical fluid extraction technology is a technology using a fluid at a critical temperature or higher and at a critical pressure or higher, and is getting attention as a new environmentally friendly clean technology that replaces conventional processes in the extraction and purification related fields including purification of medical products, food process, and petroleum chemical materials. In particular, recently, due to increasing energy source prices, environmental problems of conventional separation processes, and a high demand for special-purpose novel materials, which cannot be produced by using gas or liquid processes, industrialized countries are focused on the development of a novel process fluid technology using a supercritical fluid as a process fluid for the last 30 years, as an alternative of a conventional process using gas or liquid. As a result, the process that uses a supercritical fluid as a process fluid is rapidly introduced to all the industries, including fine chemistry, energy, environmental, and novel materials industries and replaces various conventional separation technologies.

Initially, the supercritical fluid technology for the extraction and purification of natural materials was limitedly applied to spices, cosmetic products, non-polar materials, such as fat, low-price foods, or flavoring materials. However, recently, due to the development of various phenomenological characteristics and additional technology related to this technology, the supercritical fluid technology can be applied to extract and purify polarity, small, or high-price natural medical products. There are many candidates for a supercritical fluid, and among supercritical fluids, carbon dioxide is the most often used. Carbon dioxide exists unlimitedly in the nature, and also, a great amount thereof is produced in iron-manufacturing or petroleum chemistry industries. Also, carbon dioxide is colorless and odorless, and is not harmful to the human body and is a chemically very stable material.

Also, compared to other fluids, carbon dioxide has low critical temperature (31.1° C.) and low critical pressure (7.4 MPa) and thus, is easily controlled to comply with a supercritical condition. Thus, use of carbon dioxide is environmentally friendly and enables efficient use of energy. Additionally, when this technology is used in separate and purify natural bioactive materials, problems of human body toxicity caused by an organic solvent remaining in the final products, high costs, environmental pollution due to wasted solvents, degeneration of a target component, and low extraction selectivity, which occurs when a typical process is conducted, may be addressed or compensated for.

The supercritical fluid technology using carbon dioxide has never been used to extract a bioactive component of *Portulaca oleracea* L., in particular, an omega-3 fatty acid component.

Korean Patent Registration No. 0558382 discloses a method of producing a ginkgo leaf extract by using a supercritical fluid extraction method. However, this method is different from a method of producing an omega fatty acid-containing extract from a plant by supercritical carbon dioxide extraction.

SUMMARY

The present invention is introduced in response to such an requirement, and is intended to provide a method of extracting an omega fatty acid from an omega fatty acid-containing plant by using a supercritical fluid technology, which is getting attention as a novel extraction and purification technology, wherein the method addresses problems of human body harmfulness, environmental toxicity, high costs, and low selectivity, which occurs when a typical organic solvent extraction method is used.

The present invention provides a method of producing an omega fatty acid-containing extract from an omega fatty acid-containing plant, wherein the method includes: drying an omega fatty acid-containing plant to prepare powder thereof; and extracting an omega fatty acid from the prepared plant powder using supercritical carbon dioxide as a solvent at a temperature of 20 to 70° C. and at a pressure of 150 to 350 bar.

Also, the present invention provides a health functional food including a plant-derived omega fatty acid that is extracted by using the method.

Also, the present invention provides an omega fatty acid-containing plant extract that is extracted from an omega fatty acid-containing plant by using supercritical carbon dioxide.

Also, the present invention provides a pharmaceutical composition for lowering the level of cholesterol, including a plant-derived omega-3 fatty acid that is extracted by using the method.

According to the present invention, an omega fatty acid is extracted in a high yield of 2 to 3% from omega fatty acid-containing plant by supercritical carbon dioxide. Thus, a supply amount of the omega fatty acid may be increased, and the present invention may significantly contribute to relevant studies.

Also, a method according to the present invention may allow an omega fatty acid to be extracted from *Portulaca oleracea* L., which is inexpensive and easily obtainable, at low costs.

Also, due to the use of carbon dioxide, which is not harmful to the human body, as a solvent, the method according to the present invention is environmentally friendly compared to a typical extraction method using an organic solvent, and is more simplified and requires a shorter extraction time than a typical extraction method.

Also, only with controlled temperature and pressure, a selection material (an omega-3 fatty acid, such as DHA and a linolenic acid) is extracted, and high-purity materials may be obtained. Thus, the method can be applied in industries related to health foods, pharmaceutical products, and cosmetic products.

BRIEF DESCRIPTION OF THE DRAWING

FIG. 1 shows a graph of the amount of omega-3 fatty acid of *Portulaca oleracea* L. extract according to extraction temperature and extraction pressure.

BEST MODE FOR CARRYING OUT THE INVENTION

A method of producing an omega fatty acid-containing extract from an omega fatty acid-containing plant according to an embodiment of the present invention includes a) drying an omega fatty acid-containing plant to prepare powder thereof; and b) extracting an omega fatty acid from the prepared plant powder using supercritical carbon dioxide as a solvent at a temperature of 20 to 70° C. and at a pressure of 150 to 350 bar.

Regarding the method according to the present invention, the omega fatty acid-containing plant may be any one of various plants that include an omega fatty acid, and may be, for example, *Portulaca oleracea* L. or *perilla*.

Also, regarding the method according to the present invention, the plant powder of process a) may be lyophilized plant powder. The lyophilized plant powder may contribute to an increase in extraction efficiency of the omega fatty acid, compared to plant powder that is prepared by a typical drying method.

Also, regarding the method according to the present invention, optimal conditions for the extraction of the omega fatty acid may include a temperature of 40 to 60° C. and a pressure of 200 to 300 bar, for example, a temperature of 50 to 60° C. and a pressure of 230 to 270 bar, or for example, a temperature of 54.69° C. and a pressure of 249.76 bar, in process b). When the extraction is performed under such conditions, an omega fatty acid can be extracted in highest yields.

Also, regarding the method according to the present invention, an omega fatty acid may include one or more selected from the group consisting of an omega-3 fatty acid, an omega-6 fatty acid, and an omega-9 fatty acid, and an omega-3 fatty acid may include one or more selected from the group consisting of a docosahexaenoic acid (DHA), an eicosapentaenoic acid (EPA), a docosapentaenoic acid (DPA), a linolenic acid, a stearidonic acid (SDA), and an eicosatetraenoic acid (ETA). However, the omega fatty acid and the omega-3 fatty acid may not be limited thereto. An omega-6 fatty acid may include one or more selected from the group consisting of a linoleic acid, a gamma-linolenic acid, and an arachidonic acid, but is not limited thereto. An omega-9 fatty acid may be an oleic acid, but is not limited thereto.

Also, regarding the method according to the present invention, in process b), an auxiliary solvent may be used to increase solubility of an omega fatty acid, and examples of the auxiliary solvent are ethanol, isopropanol, ethylacetate, and tetrahydrofuran, but are not limited thereto.

Also, regarding the method according to the present invention, conditions for extracting DHA and a linolenic acid, which are omega-3 fatty acids, in high yields may be slightly different from each other. Optimal conditions for extracting DHA, which is an omega-3 fatty acid, may include a temperature of 40 to 50° C. and a pressure of 220 to 280 bar, for example, a temperature of 40 to 50° C. and a pressure of 235 to 255 bar, for example, a temperature of 43 to 47° C. and a pressure of 240 to 250 bar, or for example, a temperature of 44.29° C. and a pressure of 244.55 bar. When the extraction is performed under such conditions, DHA can be extracted in the highest yield.

Also, optimal conditions for a linolenic acid, which is an omega-3 fatty acid, may include a temperature of 15 to 25° C. and a pressure of 120 to 160 bar, for example, a temperature of 15 to 25° C. and a pressure of 130 to 150 bar, for example, a temperature of 19 to 23° C. and a pressure of 135 to 145 bar, or for example, a temperature of 21.25° C. and a pressure of 138.78 bar. When the extraction is performed under such conditions, a linolenic acid can be extracted in the highest yield.

Also, a method of producing an omega-3 fatty acid-containing extract from *Portulaca oleracea* L. according to an embodiment of the present invention includes a) lyophilizing *Portulaca oleracea* L. to prepare powder thereof; and b) extracting an omega-3 fatty acid from the prepared *Portulaca oleracea* L. powder using supercritical carbon dioxide as a solvent at a temperature of 50 to 60° C. and at a pressure of 230 to 270 bar.

An example of the method of producing an omega-3 fatty acid-containing extract from *Portulaca oleracea* L. includes a) lyophilizing *Portulaca oleracea* L. to prepare powder thereof; and b) extracting an omega-3 fatty acid from the prepared *Portulaca oleracea* L. powder using supercritical carbon dioxide as a solvent at a temperature of 54.69° C. and at a pressure of 249.76 bar.

Also, the present invention provides a health functional food including a plant-derived omega fatty acid that is extracted by using the methods.

Regarding the health functional food according to the present invention, a method of extracting the plant-derived omega fatty acid included in the health functional food is the same as described above.

Examples of the food including the plant-derived omega fatty acid are a grocery, a beverage, a gum, a tea, a vitamin complex, and a health functional food.

An amount of the plant-derived omega fatty acid in a grocery or a beverage may be in a range of 0.01 to 15 wt % based on the whole food. When used in a health functional beverage, the plant-derived omega fatty acid may be included in an amount of 0.02 to 5 g, for example, 0.3 to 1 g based on 100 ml of the composition of the health functional beverage.

The health functional beverage composition according to the present invention is not limited as long as the plant-derived omega fatty acid is included as a necessary component in the above-indicated ratios, and like typical beverages, the health functional beverage composition may include as an additionally component, various flavoring agents or natural carbohydrates. Examples of the natural carbohydrates are a monosaccharide, for example, glucose, fructose, or the like; a disaccharide, for example, maltose, sucrose, or the like; and a polysaccharide, for example, a typical sugar, such as dextrin, cyclodextrin, or the like, and a sugar alcohol, such as xylitol, sorbitol, erythritol, or the like. As a favoring agent, a natural favoring agent (thaumatin, stevia extracts, for example, rebaudioside A, glycyrrhizin, or the like) and a synthetic favoring agent (saccharin, aspartame, or the like) may be advantageously used. An amount of a natural carbohydrate may be in a range of about 1 to 20 g, for example, about 5 to 12 g based on 100 ml of the health functional beverage composition according to the present invention.

Furthermore, the plant-derived omega fatty acid according to the present invention may be used together with various nutritional supplements, vitamins, minerals (electrolyte), flavoring agents, such as a syntheric flavoring agent and a natural favoring agent, a coloring agent, enhancer (cheese, chocolate, or the like), a pectic acid and salt thereof, an alginic acid and salt thereof, an organic acid, a protective colloid thickener, a pH controller, a stabilizer, a preserving agent, glycerin, alcohol, a carbonating agent used in carbonate beverages, or the like. Also, the plant-derived omega fatty acid according to the present invention may be used together with natural fruit juice, or a flesh for producing fruit juice beverages and vegetable beverages. These components may be used alone or in combination thereof, and an amount of these additives may be in a range of 0 to about 20 parts by weight based on 100 parts by weight of the extract according to the present invention.

The present invention also provides a pharmaceutical composition for decreasing the level of cholesterol which includes the extracted plant-derived omega-3 fatty acid-containing extract.

The pharmaceutical composition including the plant-derived omega-3 fatty acid according to the present invention may further include a carrier, an excipient, and a diluent which are typically used in preparing a pharmaceutical composition.

As for a pharmaceutical dose form of the plant-derived omega-3 fatty acid according to the present invention, the plant-derived omega-3 fatty acid may be used in the form of a pharmaceutically acceptable salt thereof, or used alone or in combination or set with other pharmaceutically active compounds.

The pharmaceutical composition including the plant-derived omega-3 fatty acid according to the present invention may be prepared in an oral formulation, such as powder, granule, tablet, capsule, suspension, emulsion, syrup, or aerosol, an external applicable formulation, a suppository formulation, or a sterilized injection solution formulation by using typical methods. As a carrier, an excipient, and a diluent which are included in a composition including the plant-derived omega-3 fatty acid, various compounds or mixtures including lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, a mineral oil, or the like may be used. For the preparation into various formulations, a diluent or an excipient, such as a typical filler, a bulking agent, a binder, a wetting agent, a disintegrating agent, or a surfactant, may be used. Examples of a solid formulation for oral administration are tablets, pills, powder, granules, and capsules, and these solid formulations are prepared by mixing the fermented liquid with at least one excipient selected from starch, calcium carbonate, sucrose, lactose, and gelatin. In addition to the expedient, a lubricant, such as magnesium stearate, or talc, is used. As a liquid formulation for oral administration, suspension, an oral liquid dosage form, emulsion, syrup, or the like may be used, and in addition to water, which is often used, and liquid paraffin, various other excipients, for example, a wetting agent, a sweetener, a flavoring agent, or a preserving agent may be included. As a formulation for oral administration, a sterilized liquid solution, a non-aqueous solvent, a suspension, an oil, a lyophilized preparation, a suppository formulation, or the like may be used. As a non-aqueous solvent or a suspension, propylene glycol, a plant oil, such as olive oil, an injectable ester, such as ethylolate, or the like may be used. As a support for suppositories, witepsol, polyethylene glycol, tween 61, cocoa butter, laurinum, glycerogelatin, or the like may be used.

A dosage of the plant-derived omega-3 fatty acid may vary according to the state, body weight, seriousness degree of disease of a patient, a drug formulation, an administration path, and an administration period, and may be appropriately determined by one of ordinary skill in the art. However, to obtain high effects, a daily dosage of the plant-derived omega-3 fatty acid may be in a range of 0.0001 to 100 mg/kg, for example, 0.001 to 100 mg/kg per day. The dosage may all be administered once a day, or several divided dosages may be administered daily. The dosages do not limit the scope of the present invention in any aspect.

The plant-derived omega-3 fatty acid according to the present invention may be administered to mammals, such as rats, mice, livestock, or humans through various paths. The administration may be obvious to one of ordinary skill in the art, and may be, for example, an oral administration, or a rectal, intravenous, muscular, subcutaneous, endocervical septum, or intracerebroventricular injection administration.

Also, the present invention provides an omega fatty acid-containing plant extract that is prepared by extracting an omega fatty acid-containing plant by using supercritical carbon dioxide, wherein an amount of omega-3 fatty acid is 2 wt % or more based on the total weight of the extract. In the extract, the amount of the omega-3 fatty acid may be, based on the total weight of the extract, 2.5 wt % or more, for example, 2.6 wt % or more.

Also, the present invention provides an omega fatty acid-containing plant extract that is prepared by extracting an omega fatty acid-containing plant by using supercritical carbon dioxide, wherein an amount of omega-3 fatty acid is 55 wt % or more based on the total weight of a fatty acid in the extract. For example, in the extract, the amount of the omega-3 fatty acid may be 60 wt % or more based on the total weight of a fatty acid in the extract.

Hereinafter, embodiments of the present invention are described in detail below. However, the embodiments are presented for illustrative purpose only, and do not limit the scope of the present invention.

1. Raw Materials

Perilla was supplied by Korea Research Institute of Bioscience & Biotechnology, and *Portulaca oleracea* L. powder that was prepared by using a typical drying method and *Portulaca oleracea* L. powder that was prepared by a lyophilizing method were supplied by Sungin Food Co., Ltd located in San-cheong kun.

2. Supercritical Carbon Dioxide Extraction Method

This extraction test was performed using a batch-type supercritical carbon dioxide extraction apparatus (KBNE-01, 02 SYSTEM). The extraction was performed as follows: saturated pressure-state carbon dioxide (purity 99.9%) was passed through a cooler (−10° C.) to remove bubbles, and then, pressed by using a liquid constant pressure pump (PU-2088-CO2 PLUS, Jasco) until the pressure reached a predetermined pressure. Before loading from the pump to a reactor, carbon dioxide, which is an extraction solvent, was preheated in advance in a constant-temperature bath at an extraction temperature which was set in advance, and the extraction temperature of the reactor is detected by a thermocouple to control the extraction temperature, thereby maintaining the inner temperature constantly. The total pressure inside the extraction apparatus was maintained constant by attaching a pressure controlling pump and one a pressure controller to the extraction apparatus to prevent any change in conditions inside the extraction apparatus resulting from an instant pressure change. A fatty matter extracted from the reactor was guided to pass a metering valve and then collected through a letter 'T'-shaped glass tube, and a fluid amount was measured by using a dry flow-meter (DC-2, Shinagawa seik).

3. Fatty Acid Analysis

The fatty matter extracted from supercritical carbon dioxide was methylated according to an AOAC method, and then analyzed by using a GC-FID (Hewlett Packard 5890). A pretreatment was performed as follows. 0.05 g of the extract was added to a round flask equipped with a reflux cooling tube, and then 3 mL of 0.5N NaOH in methanol was added thereto, followed by heating in a double boiler at a temperature of 75° C. for 30 minutes. Following the heating, the reaction solution was left to sit for cooling for 10 minutes, and then, 3 ml of $BF_3$ (Supelcotm) in methanol was added thereto, followed by heating in a double boiler at a temperature of 75° C. for 25 minutes, and then the resultant product was left to sit for cooling for 10 minutes. Following the cooling, 3 ml of hexane and 1 ml of 10% NaCl solution were added thereto, followed by shaking for 30 seconds. The composition of a fatty acid was analyzed by using nGC-FID, and compared with peaks of a reference material (FAME MIX., DHA, EPA standard) to quantify the fatty acid.

4. Statistic Analysis

An extraction condition test was performed as follows. A central composition design was performed to set experimental ranges of a factor considered as an important independent variable (Xi) in an extraction process, that is, an extraction temperature ($X_1$) and an extraction pressure ($X_2$), and the experimental ranges of the respective factors were coded as 5 levels (Table 1), and extraction was performed under 10 extraction conditions constructed according to the central composite design. Also, a dependent variable (Yn) which is affected by the independent variables, for example, an extraction amount of omega-3 was measured and the measurement value was used for regression analyst.

TABLE 1

Test design of supercritical carbon dioxide extraction conditions

| Extraction condition | −2 | −1 | 0 | 1 | 2 |
|---|---|---|---|---|---|
| $X_1$ Temperature (° C.) | 35 | 45 | 55 | 65 | 75 |
| $X_2$ Pressure (bar) | 100 | 160 | 220 | 280 | 340 |

Prediction made based on a regression equation was conducted by using a statistical analysis system (SAS) program, and an optimal extraction condition was predicted using an omega-3 fatty acid extraction amount.

Example 1

Analysis of Fatty Acid Contained in Perilla Supercritical Extract

A fatty acid was extracted from *perilla* by using supercritical carbon dioxide under temperature and pressure conditions shown in Table 2 below, and the fatty acid extract was analyzed. Results thereof are shown in Table 2 below. From the results shown in Table 2, it was confirmed that a linolenic acid, which is an omega-3 fatty acid, accounted for about 60% of the total weight of the fatty acid.

TABLE 2

Analysis of fatty acid contained in perilla supercritical extract

| Composition | R.t (min) | 45° C., 100 bar (%) | 45° C., 200 bar (%) | 45° C., 300 bar (%) | 65° C., 300 bar (%) |
|---|---|---|---|---|---|
| Palmitic acid | 23.06 | 8.0 | 7.6 | 6.7 | 6.8 |
| Stearic acid | 26.21 | 1.9 | 1.9 | 2.0 | 2.0 |
| Oleic acid | 27.28 | 15.3 | 15.3 | 15.6 | 16.0 |
| Linoleic acid | 28.80 | 14.9 | 14.7 | 14.6 | 14.6 |
| Linolenic acid | 29.93 | 59.9 | 60.5 | 61.1 | 60.5 |

Example 2

Extraction Efficiency of Omega-3 Fatty Acids from *Portulaca oleracea* L. Extract The extraction efficiency of omega-3 fatty acids from extracts was analyzed with respect to a method of drying *Portulaca oleracea* L. and an extraction method. In this experiment, extraction efficiencies of a typically dried *Portulaca oleracea* L. soxhlet extract, a typically dried *Portulaca oleracea* L. supercritical extract, and a lyophilized *Portulaca oleracea* L. supercritical extract were analyzed.

TABLE 3

Composition of fatty acid contained in *Portulaca oleracea* L. extract.

| Fatty acids | Typically dried sample Soxhlet | Typically dried sample supercriticality | Lyophilized sample supercriticality |
|---|---|---|---|
| Lauric acid | 0.21% | 0.00% | 0.00% |
| Myristic acid | 0.79% | 0.39% | 0.46% |
| Myristoleic acid | 0.00% | 0.44% | 0.30% |
| Palmitic acid | 16.57% | 18.37% | 16.10% |
| Palmitoleic acid | 0.71% | 1.09% | 0.00% |
| Stearic acid | 2.20% | 4.11% | 3.13% |
| Oleic acid | 13.74% | 10.11% | 8.24% |
| Elaidic acid | 1.53% | 1.30% | 1.31% |
| Linolelaidic acid | 59.73% | 32.77% | 36.60% |
| r-Linolenic acid | 3.45% | 26.44% | 28.79% |
| Linolenic acid | 0.38% | 1.29% | 1.19% |
| Heneicosanoec acid | 0.14% | 0.29% | 0.00% |
| Arachidonic acid | 0.33% | 1.36% | 1.20% |
| Eicosapentaenoic acid (EPA) | 0.22% | 1.38% | 1.14% |
| Docosahexaenoic acid (DHA) | 0.00% | 0.66% | 1.53% |
| Total | 100.00% | 100.00% | 100.00% |

GC-MS analysis was performed on the extracts. Regarding the extraction efficiency of the omega-3 fatty acid, such as a linolenic acid, EPA, and DHA, the supercritical extraction produced higher extraction efficiency than the soxhlet extraction, and as for a drying method, lyophilizing drying produced higher extraction efficiency than typical drying. In Table 3, regarding a linolenic acid, EPA, and DHA, in the case of linolenic acid and EPA, a typically dried sample supercriticality showed slightly higher extraction efficiency than a lyophilized sample supercriticality, and in the case of DHA, the lyophilized sample supercriticality showed substantially higher extraction efficiency than the typically drying sample supercriticality. Also, regarding the total extraction yield of linolenic acid, EPA, and DHA, which are omega-3 fatty acids, the lyophilizing produced higher extraction efficiency than typical drying.

Example 3

Setting of Optimal Conditions According to DHA Extraction Amount

To determine an optimal condition for the extraction from *Portulaca oleracea* L, extracting was performed under 10 extraction conditions designed by the central composite design while using the extraction temperature and the extraction pressure as independent variables, and DHA amounts in the obtained extract were measured, and results thereof are shown in Table 4. Optimal extraction conditions predicted through regression (Table 5) obtained by response surface methodology are shown in Table 6 below.

TABLE 4

DHA amounts of extracts under different extraction conditions constructed by central composite design

| Experiment No | Temperature (° C.) | Pressure (bar) | DHA Content (mg/g) | $CO_2$ density |
|---|---|---|---|---|
| 1 | 65(1) | 340(2) | 0.00 | 0.84010 |
| 2 | 65(1) | 160(−1) | 12.37 | 0.59490 |
| 3 | 45(−1) | 340(2) | 5.29 | 0.91344 |
| 4 | 45(−1) | 160(−1) | 10.69 | 0.76180 |
| 5 | 35(−2) | 220(0) | 7.88 | 0.88201 |
| 6 | 55(0) | 100(−2) | 0.00 | 0.32442 |
| 7 | 55(0) | 220(0) | 5.93 | 0.78184 |
| 8 | 55(0) | 220(0) | 8.40 | 0.78184 |
| 9 | 75(+2) | 220(0) | 4.83 | 0.66815 |
| 10 | 55(0) | 340(+2) | 5.03 | 0.87720 |

TABLE 5

Regression equation obtained by response surface methodology

| Response | Second order polynominals |
|---|---|
| DHA content (mg/g) | $Y_{DHA} = -45.156521 + 0.893466X_1 + 0.286874X_2 - 0.005022X_1^2 - 0.001835X_1X_2 - 0.000420X_2^2$ |

TABLE 6

Predicted optimal extraction conditions of DHA

| Response | $X_1$ (° C.) | $X_2$ (bar) | Maximum (mg/extract g) | Morphology |
|---|---|---|---|---|
| DHA content | 44.286 | 244.545 | 9.704 | Maximum |

As a result, it was confirmed that DHA was the most efficiently extracted from *Portulaca oleracea* L. by supercritical carbon dioxide extraction at a temperature of 44.286° C. and at a pressure 244.545 bar.

Example 4

Setting of Optimal Conditions According to Linolenic Acid Extraction Amount

To determine an optimal condition for the extraction from *Portulaca oleracea* L, extracting was performed under 10 extraction conditions designed by the central composite design while using the extraction temperature and the extraction pressure as independent variables, and amounts of a linolenic acid in the obtained extract were measured, and results thereof are shown in Table 7. Optimal extraction conditions predicted through regression (Table 8) obtained by response surface methodology are shown in Table 9 below.

TABLE 7

Amounts of linolenic acid contained in an extract under different extraction conditions designed by central composite design

| Experiment No | Extraction Conditions | | Linolenic acid Content (mg/g) | $CO_2$ density |
|---|---|---|---|---|
| | Temperature (° C.) | Pressure (bar) | | |
| 1 | 65(1) | 340(2) | 22.10 | 0.84010 |
| 2 | 65(1) | 160(−1) | 12.27 | 0.59490 |
| 3 | 45(−1) | 340(2) | 11.27 | 0.91344 |
| 4 | 45(−1) | 160(−1) | 13.49 | 0.76180 |
| 5 | 35(−2) | 220(0) | 14.72 | 0.88201 |
| 6 | 55(0) | 100(−2) | 0.00 | 0.32442 |
| 7 | 55(0) | 220(0) | 10.38 | 0.78184 |
| 8 | 55(0) | 220(0) | 18.66 | 0.78184 |
| 9 | 75(+2) | 220(0) | 10.49 | 0.66815 |
| 10 | 55(0) | 340(+2) | 14.49 | 0.87720 |

TABLE 8

Regression equation obtained by response surface methodology

| Response | Second order polynominals |
|---|---|
| Linolenic acid content (mg/g) | $Y_{Linolenic\ acid} = 14.241001 − 0.324217X_1 + 0.043357X_2 − 0.005145X_1^2 + 0.003912X_1X_2 − 0.000456X_2^2$ |

TABLE 9

Predicted optimal extraction conditions of linolenic acid

| Response | $X_1$ (° C.) | $X_2$ (bar) | Maximum (mg/extract g) | Morphology |
|---|---|---|---|---|
| Linolenic acid content | 21.250 | 138.778 | 13.805 | Saddle point |

As a result, it was confirmed that linolenic acid was the most efficiently extracted from *Portulaca oleracea* L. by supercritical carbon dioxide extraction at a temperature of 21.250° C. and at a pressure of 138.778 bar.

Example 5

Setting of Optimal Conditions According to Omega-3 Fatty Acid Extraction Amounts To determine an optimal condition for the extraction from *Portulaca oleracea* L, extracting was performed under 10 extraction conditions designed by the central composite design while using the extraction temperature and the extraction pressure as independent variables, and amounts of an omega-3 fatty acid in the obtained extract were measured, and results thereof are shown in Table 10. Optimal extraction conditions predicted through regression (Table 11) obtained by response surface methodology are shown in FIG. 1 and Table 12 below.

TABLE 10

Amounts of omega-3 fatty acid contained in an extract under different extraction conditions designed by central composite design

| Experiment No | Extraction Condition | | Omega-3 Content (mg/g) | $CO_2$ density |
|---|---|---|---|---|
| | Temperature (° C.) | Pressure (bar) | | |
| 1 | 65(1) | 340(2) | 22.10 | 0.84010 |
| 2 | 65(1) | 160(−1) | 30.04 | 0.59490 |
| 3 | 45(−1) | 340(2) | 16.56 | 0.91344 |
| 4 | 45(−1) | 160(−1) | 24.18 | 0.76180 |
| 5 | 35(−2) | 220(0) | 22.60 | 0.88201 |
| 6 | 55(0) | 100(−2) | 0.00 | 0.32442 |
| 7 | 55(0) | 220(0) | 16.31 | 0.78184 |
| 8 | 55(0) | 220(0) | 27.06 | 0.78184 |
| 9 | 75(+2) | 220(0) | 15.32 | 0.66815 |
| 10 | 55(0) | 340(+2) | 19.52 | 0.87720 |

TABLE 11

Regression equation obtained by response surface methodology

| Response | Second order polynominals |
|---|---|
| omega-3 content (mg/g) | $Y_{omega-3} = −48.358096 + 0.957253X_1 + 0.390795X_2 − 0.011013X_1^2 + 0.000991X_1X_2 − 0.000891X_2^2$ |

TABLE 12

Predicted optimal extraction conditions for omega-3 fatty acid

| Response | $X_1$ (° C.) | $X_2$ (bar) | Maximum (mg/extract g) | Morphology |
|---|---|---|---|---|
| omega-3 content | 54.693 | 249.761 | 26.6222 | Maximum |

As a result, it was confirmed that linolenic acid was the most efficiently extracted from *Portulaca oleracea* L. by supercritical carbon dioxide extraction at a temperature of 54.693° C. and at a pressure of 249.761 bar.

The extracts according to the present invention are prepared according to preparation examples presented below, and the following preparation examples are used for illustrative purpose only and the present invention is not limited thereto.

Preparation Example 1

Health Functional Foods Including Omega Fatty Acid-Containing Extract

This experiment was performed to produce a health beverage food that allows consumers to easily intake an omega fatty acid-containing extract prepared by using the method according to the present invention. In detail, 1 part by weight of the omega fatty acid-containing extract according to the present invention, 1 part by weight of a citric acid, 5 parts by weight of oligosaccharide, and 5 parts by weight of taurine were mixed and then, water was added thereto until the total amount of the resultant mixture reached 100 mL, followed by filling in a bottle and sterilizing, thereby completing the production of a health beverage including the omega fatty acid-containing extract.

Preparation Example 2

Pharmaceutical Composition Including Omega-3 Fatty Acid-Containing Extract

A pharmaceutical composition for lowering the level of cholesterol which includes the omega-3 fatty acid-containing extract according to the present invention was formulated according to the following preparation examples.

Preparation Example 1

Tablet Formulation 200 mg of omega-3 fatty acid-containing extract according to the present invention
100 mg of lactose
100 mg of starch
an appropriate amount of stearic acid magnesium
These components were mixed and formulated as tablets according to a typical tablet preparation method.

Preparation Example 2

Capsule Formulation 100 mg of omega-3 fatty acid-containing extract according to the present invention
50 mg of lactose
50 mg of starch
2 mg of talc
an appropriate amount of stearic acid magnesium
These components were mixed and the mixture was filled in a gelatin capsule, according to a typical capsule preparation method.

The invention claimed is:

1. A method of producing an omega fatty acid-containing extract from an omega fatty acid-containing plant, the method comprising:
    a) drying an omega fatty acid-containing plant to prepare powder thereof; and
    b) extracting an omega fatty acid from the prepared plant powder using supercritical carbon dioxide as a solvent,
    wherein (i) the extracting the omega fatty acid comprises extracting DHA from the prepared plant powder using the supercritical carbon dioxide as the solvent at a temperature of 40 to 50° C. and at a pressure of 220 to 280 bar; or
    (ii) the process a) comprises lyophilizing *Portulaca oleracea* L. to prepare the powder thereof; and the process b) comprises extracting an omega-3 fatty acid from the prepared *Portulaca oleracea* L. powder using the supercritical carbon dioxide as the solvent at a temperature of 50 to 60° C. and a pressure of 230 to 270 bar.

2. The method of claim 1, wherein the omega fatty acid-containing plant is *Portulaca oleracea* L. or *perilla*.

3. The method of claim 1, wherein the plant powder in process a) is lyophilized plant powder.

4. The method of claim 1, wherein in process b), an auxiliary solvent is additionally used, and the auxiliary solvent is ethanol, isopropanol, ethylacetate, or tetrahydrofurane.

5. The method of claim 1, wherein the extracting the omega fatty acid comprises extracting the DHA from the prepared plant powder using the supercritical carbon dioxide as the solvent at the temperature of 40 to 50° C. and at the pressure of 220 to 280 bar.

6. The method of claim 1, wherein the process a) comprises lyophilizing the *Portulaca oleracea* L. to prepare the powder thereof; and the process b) comprises extracting the omega-3 fatty acid from the prepared *Portulaca oleracea* L. powder using the supercritical carbon dioxide as the solvent at the temperature of 50 to 60° C. and the pressure of 230 to 270 bar.

7. The method of claim 1, wherein the omega fatty acid-containing plant extract produced having an amount of the omega fatty acid that is 2 wt % or more based on the total weight of the extract.

8. The method of claim 1, wherein the omega fatty acid-containing plant extract produced having an amount of the omega fatty acid that is 55 wt % or more based on the total weight of a fatty acid in the extract.

* * * * *